United States Patent
Li et al.

(10) Patent No.: US 11,583,508 B2
(45) Date of Patent: Feb. 21, 2023

(54) USE OF MITOXANTRONE LIPOSOME FOR TREATING NON-HODGKIN'S LYMPHOMA

(71) Applicant: CSPC ZHONGQI PHARMACEUTICAL TECHNOLOGY (SHIJIAZHUANG) CO., LTD., Hebei (CN)

(72) Inventors: Chunlei Li, Hebei (CN); Yueying Peng, Hebei (CN); Kun Lou, Hebei (CN); Yajuan Wang, Hebei (CN); Yumei Wang, Hebei (CN); Shan Chen, Hebei (CN); Zhibin Meng, Hebei (CN); Jianfei Xue, Hebei (CN); Jing Yuan, Hebei (CN); Hongmei Luo, Hebei (CN); Xuekun Yao, Hebei (CN); Shixia Wang, Hebei (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 15 days.

(21) Appl. No.: 17/258,801

(22) PCT Filed: Jul. 10, 2019

(86) PCT No.: PCT/CN2019/095396
§ 371 (c)(1),
(2) Date: Jan. 8, 2021

(87) PCT Pub. No.: WO2020/011189
PCT Pub. Date: Jan. 16, 2020

(65) Prior Publication Data
US 2021/0267915 A1 Sep. 2, 2021

(30) Foreign Application Priority Data
Jul. 11, 2018 (CN) .......................... 201810756315.7

(51) Int. Cl.
*A61K 31/136* (2006.01)
*A61P 35/00* (2006.01)
*A61K 9/00* (2006.01)
*A61K 9/127* (2006.01)

(52) U.S. Cl.
CPC .......... *A61K 31/136* (2013.01); *A61K 9/0019* (2013.01); *A61K 9/127* (2013.01); *A61P 35/00* (2018.01)

(58) Field of Classification Search
None
See application file for complete search history.

(56) References Cited

U.S. PATENT DOCUMENTS

| 2003/0219476 A1* | 11/2003 | Ahmad ................ A61K 31/136 514/649 |
| 2009/0081203 A1* | 3/2009 | Pietronigro ....... A61K 39/39558 514/323 |
| 2016/0038460 A1* | 2/2016 | Sacchettini ........ A61K 31/7068 435/375 |
| 2016/0235671 A1* | 8/2016 | Li ........................ A61K 31/136 |

FOREIGN PATENT DOCUMENTS

| CN | 101209243 | 7/2008 |
| CN | 103622909 | 3/2014 |
| EP | 2123260 B1 | 2/2013 |
| WO | 2008080367 | 7/2008 |

OTHER PUBLICATIONS

Mainwaring et al (Blood, May 15, 2001, 97(10), 2991-2997) (Year: 2001).*
Silver et al (J Clin Oncol, May 1991, 9(5), 754-61) (Year: 1991).*
U.S. National Library of Medicine (https://clinicaltrials.gov/ct2/show/NCT02856685) (Year: 2016).*
Armitage, The Aggressive Peripheral T-cell Lymphomas, American Journal of Hematology, vol. 92, No. 7, Jul. 2017, pp. 706-715.
Blystad et al., High-dose Therapy with Autologous Stem Cell Transplantation in Patients with Peripheral T Cell Lymphomas, Bone Marrow Transplantation, vol. 27, No. 7, Apr. 2001, pp. 711-716.
Chao, Treatment Challenges in the Management of Relapsed or Refractory Non-hodgkin's Lymphoma—Novel and Emerging Therapies, Cancer Management and Research, vol. 5, 2013, pp. 251-269.
Coiffier et al., Romidepsin for the Treatment of Relapsed/refractory Peripheral T-cell Lymphoma: Pivotal Study Update Demonstrates Durable Responses, Journal of Hematology & Oncology, vol. 7, No. 11, Jan. 23, 2014, pp. 1-9.
Corradini et al., Long-term Follow-up of Patients with Peripheral T-cell Lymphomas Treated Up-front with High-dose Chemotherapy Followed by Autologous Stem Cell Transplantation, Leukemia, vol. 20, No. 9, Sep. 2006, pp. 1533-1538.
Moskowitz et al., How I treat the Peripheral T-cell Lymphomas, Blood, vol. 123, No. 17, Apr. 24, 2014, pp. 2636-2644.
Niitsu et al., Phase II Study of the Irinotecan (CPT-11), Mitoxantrone and Dexamethasone Regimen in Elderly Patients with Relapsed or Refractory Peripheral T-cell Lymphoma, Cancer Science, vol. 98, No. 1, Jan. 2007, pp. 109-112.
O'Connor et al., Belinostat in Patients with Relapsed or Refractory Peripheral T-Cell Lymphoma: Results of the Pivotal Phase II BELIEF (CLN-19) Study, Journal of Clinical Oncology, vol. 33, No. 23, Aug. 10, 2015, pp. 2492-2499.

(Continued)

*Primary Examiner* — Gollamudi S Kishore
(74) *Attorney, Agent, or Firm* — Kilpatrick Townsend & Stockton LLP

(57) ABSTRACT

Disclosed is a use of a liposomal pharmaceutical preparation of mitoxantrone in the preparation of a medicament for treating lymphoma, wherein the lymphoma is preferably non-Hodgkin's lymphoma, further preferably aggressive non-Hodgkin's lymphoma, more preferably diffuse large B-cell lymphoma or peripheral T-cell lymphoma, and more further preferably relapsed or refractory diffuse large B-cell lymphoma or peripheral T-cell lymphoma. The mitoxantrone liposomes are used as single anti-tumor therapeutic agent without being combined with other anti-tumor agents.

15 Claims, No Drawings

(56) References Cited

OTHER PUBLICATIONS

O'Connor et al., Pralatrexate in Patients with Relapsed or Refractory Peripheral T-Cell Lymphoma: Results from the Pivotal PROPEL Study, Journal of Clinical Oncology, vol. 29, No. 9, Mar. 20, 2011, pp. 1182-1189.
Shi et al., Results from a Multicenter, Open-label, Pivotal Phase II Study of Chidamide in Relapsed or Refractory Peripheral T-cell Lymphoma, Annals of Oncology, vol. 26, No. 8, Aug. 2015, pp. 1-6.
International Application No. PCT/CN2019/095396, International Preliminary Report on Patentability dated Jan. 21, 2021, 11 pages (4 pages of Original Document and 7 pages of English Translation).
International Application No. PCT/CN2019/095396, International Search Report and Written Opinion dated Sep. 20, 2019, 16 pages (9 pages of Original Document and 7 pages of English Translation).
Extended European Search Report in EP 19833348.6, dated Jun. 18, 2022, 10 pages.

* cited by examiner

USE OF MITOXANTRONE LIPOSOME FOR TREATING NON-HODGKIN'S LYMPHOMA

CROSS REFERENCE WITH RELATED PATENT APPLICATIONS

This patent application requires the priority of the Chinese patent application No. 201810756315.7, titled "Use of Mitoxantrone Hydrochloride Liposome for treating Non-Hodgkin's Lymphoma", submitted to the Chinese Patent Office on Jul. 11, 2018, the entire content of which is incorporated in this application by reference.

This patent application also quotes the Chinese patent application 200610102339.8 filed on Dec. 29, 2006 and the PCT application WO2008/080367 A1 filed on Dec. 29, 2007, the disclosures of which are incorporated herein by reference in their entirety.

TECHNICAL FIELD

The invention belongs to the field of anti-tumor, and specifically relates to a use of mitoxantrone liposomes for treating lymphoma, especially diffuse large B-cell lymphoma and peripheral T-cell lymphoma.

BACKGROUND ART

1. Background of Disease

Malignant lymphoma (ML) is a general term for a large group of complex malignancies of the lymphoid hematopoietic system, divided into two categories: Hodgkin's lymphoma (HL) and non-Hodgkin's lymphoma (NHL).

NHL is a group of proliferative and malignant lymphomas of heterogeneous lymphoid tissue with different clinical manifestations and treatment responses. NHL can be further divided into two categories: aggressive lymphomas and indolent lymphomas according to the progression speed and degree of malignancy. Aggressive lymphomas mainly include diffuse large B-cell lymphoma (DLBCL), mantle cell lymphoma (MCL), Burkitt's lymphoma, transformed follicular lymphoma (TFL) and peripheral T-cell lymphoma (PTCL), etc. (Pralatrexate in Patients With Relapsed or Refractory Peripheral T-Cell Lymphoma: Results From the Pivotal PROPEL Study, J Clin Oncol, O'Connor et al., 2011, Vol. 29, pp. 1182-1189).

Most NHLs derive from B cells, and diffuse large B-cell lymphoma is the most common subtype of NHLs. In European and American countries, the incidence of DLBCL accounts for about 30% or more of NHLs (The aggressive peripheral T-cell lymphomas, Journal of Am J Hematol, Joe Shapiro et al., 2017, Vol. 92, pp. 706-715. How I treat the peripheral T-cell lymphomas, Journal of BLOOD, Alison J. Moskowitz et al., 2014, Vol. 123, pp. 2636-2644). According to the US National Comprehensive Cancer Network (NCCN) guidelines (2016) for treatment, chemotherapy regimens containing anthracyclines such as RCHOP (rituximab-cyclophosphamide+adriamycin+vincristine+prednisone) are still considered as first-line therapeutic regimens for treating DLBCL.

About one-third of DLBCL is refractory or relapsed. Currently, as for relapsed or refractory DLBCL, many regimens for salvage treatment in clinical practice are available, but there is still no standard regimen. Although salvage combination chemotherapy regimens with ICE (ifosfamide+carboplatin+etoposide), R-ESHAP (rituximab-etoposide+methylprednisolone+cytarabine+cisplatin) and the like (Treatment challenges in the management of relapsed or refractory non-Hodgkin's lymphoma—novel and emerging therapies, Journal of Cancer Management and Research, Mark P Chao et al., 2013, Vol. 5, pp. 251-269) are available, an effective monotherapy regimen is rare. In addition, most patients with relapsed or refractory DLBCL have been treated with multi-line chemotherapy regimens. Patients with poor systemic condition, especially low bone marrow function, are mostly intolerable to continuation in receiving multi-cycle combination chemotherapy regimen. Therefore, effective monotherapy is a preferred therapeutic regimen for relapsed or refractory DLBCL.

PTCL is a group of malignant diseases of lymphatic system originating from post-thymic mature T-lymphocytes, which accounts for about 10%-20% of all non-Hodgkin's lymphoma cases and has a higher incidence in Asia (The aggressive peripheral T-cell lymphomas, Journal of Am J Hematol, Joe Shapiro et al., 2017, Vol. 92, pp. 706-715. How I treat the peripheral T-cell lymphomas, Journal of Blood, Alison J. Moskowitz et al., 2014, Vol. 123, pp. 2636-2644). Anthracycline-based therapies are often used as first-line therapeutic regimens for PTCL, such as CHOP (cyclophosphamide+adriamycin+vincristine+prednisone), but these therapeutic regimens do not allow PTCL subjects to achieve sustained remission (How I treat the peripheral T-cell lymphomas, Journal of Blood, Alison J. Moskowitz et al., 2014, Vol. 123, pp. 2636-2644). According to the US National Comprehensive Cancer Network (NCCN) guidelines (2016) for treatment, anthracycline-containing chemotherapy (CHOP) is still considered as a first-line therapeutic regimen, and the recommended monotherapies for treating relapsed/refractory PTCL (RR-PTCL), including pralatrexate (Pralatrexate in Patients With Relapsed or Refractory Peripheral T-Cell Lymphoma: Results From the Pivotal PROPEL Study, J Clin Oncol, O'Connor et al., 2011, Vol. 29, pp. 1182-1189), romidepsin (Romidepsin for the treatment of relapsed/refractory peripheral T-cell lymphoma: pivotal study update demonstrates durable responses, Journal of Hematology&Oncology, Coiffier et al., 2014, Vol 7, pp. 1-9), belinostat (Belinostat in Patients With Relapsed or Refractory Peripheral T-Cell Lymphoma: Results of the Pivotal Phase II BELIEF (CLN-19) Study, Journal of Clinical Oncology, O'Connor et al., 2015, Vol. 33, pp. 2492-2499), chidamide (Results from a multicenter, open-label, pivotal phase II study of chidamide in relapsed or refractory peripheral T-cell lymphoma, Annals of Oncology, Y. Shi et al., 2015, Vol. 00, pp. 1-6) and other HDAC inhibitors are used as second-line treatments. The above histone deacetylase inhibitors (HDAC inhibitors) are characterized by a low overall remission rate (ORR, only about 30%), which means that nearly 70% of patients who failed in the first-line treatment fail to benefit from treatment with HDAC inhibitors. The ORR of each HDAC inhibitor is shown in the table below.

|  | Pralatrexate | Romidepsin | Belinostat | Chidamide |
|---|---|---|---|---|
| Primary endpoint: (ORR, %) | 27 | 26 | 25.8 | 27.8 |

2. Comparison of Mechanisms

Mitoxantrone hydrochloride is a widely used drug in clinical practice at present, which was first synthesized and shown to have anti-tumor activities by U.S. researchers in 1979. It was first marketed in the United States and Canada in 1984, and was approved for manufacture by the U.S. Food and Drug Administration at the end of 1987. It has been used in more than 30 countries so far, and was officially produced and marketed in China in February 1991. The FDA-approved indications are multiple sclerosis, prostate cancer and acute myeloid leukemia. Its clinical application areas mainly include malignant lymphoma, breast cancer and acute myeloid leukemia, lung cancer, melanoma, soft tissue sarcoma, multiple myeloma, liver cancer, colorectal cancer, kidney cancer, prostate cancer, endometrial cancer, testicular tumor, ovarian cancer and head and neck cancer, against which it has certain efficacy.

Mitoxantrone is an anti-tumor agent belonging to anthraquinone antibiotic class, the main mechanism of action of which is intercalation into deoxyribonucleic acid through hydrogen bonding, leading to crosslinks and breaks of DNA structure. Mitoxantrone can interfere with RNA and also is a potent inhibitor of topoisomerase II. It has a cytocidal effect on both proliferating/spreading cancer cells as well as non-proliferating/spreading cancer cells in human body, and is a cell cycle nonspecific agent.

HDAC inhibitors inhibit the proliferation of tumor cells and induce cell differentiation and (or) apoptosis by paths such as increasing the degree of acetylation of histones in cells and increasing the expression levels of genes such as p21. Histone deacetylase inhibitors have become a new focus of research on tumor targeting therapy, and their inhibitory effects on tumor cell migration, invasion and metastasis and anti-tumor angiogenesis effects have also been confirmed. The mechanisms of mitoxantrone as a chemotherapy drug and the targeted drug HDAC inhibitor both support the treatment of PTCL, but their mechanisms of action are different. The efficacy of the chemotherapy drugs can be enhanced by increasing the dosage, while the targeted drugs have the phenomenon of target saturation, namely the efficacy is not necessarily increased by increasing the dosage.

3. Therapeutic Regimen

In the prior art, in the treatment of DLBCL and PTCL, the therapeutic regimens with mitoxantrone are mostly multi-drug combination therapeutic regimens.

According to the US National Comprehensive Cancer Network (NCCN) guidelines (2016) for treatment, as far as the therapeutic regimen for DLBCL is concerned, combination regimens containing mitoxantrone only have a second-line therapeutic regimen MINE (mesna+ifosfamide+ mitoxantrone+etoposide).

It has been reported that the relapsed or refractory peripheral T-cell lymphoma in elderly patients (aged 70-79 years) was treated with CMD regimen (CPT-11-irinotecan, mitoxantrone [MIT], dexamethasone [DEX]) (Phase II study of the irinotecan (CPT-11), mitoxantrone and dexamethasone regimen in elderly patients with relapsed or refractory peripheral T-cell lymphoma, Journal of Cancer Sci, Nozomi Niitsu et al., 2007, Vol. 98, pp. 109-112). A total of 30 patients were enrolled in the study, and the ORR was 60% among patients who were evaluable for efficacy. The dosage of mitoxantrone being used was 8 mg/m$^2$, 3 weeks per cycle for a total of 6 cycles. In this study, 18 patients (60%) developed grades 3-4 hematological toxicity. 8 patients (27%) developed grade 4 neutropenia despite the use of leucocyte increasing agents (G-CSF). 5 patients (16.7%) developed grades 3-4 thrombocytopenia. 2 patients (6.7%) developed grade 3 erythropenia.

It has been reported that 2 phase II trials were used (Long-term follow-up of patients with peripheral T-cell lymphomas treated up-front with high-dose chemotherapy followed by autologous stem cell transplantation, Journal of Leukemia, P Corradini et al., 2006, Vol. 20, pp. 1533-1538). In the first trial, 32 patients received an APO regimen (doxorubicin+vincristine+prednisone) for 2 cycles, followed by a DHAP regimen (cisplatin+cytarabine+dexamethasone) for 2 cycles, and conditionally received high-dose mitoxantrone (60 mg/m$^2$) combined with melphalan (180 mg/m$^2$) after bone marrow autotransplantation. The report did not disclose which patients were eligible for that chemotherapy regimen after transplantation, and the use of this regimen after transplantation could not reflect the efficacy of chemotherapy alone. In the second trial, 30 patients received MACOP (methotrexate+doxorubicin+cyclophosphamide+ vincristine+bleomycin) regimen for 8 weeks, then received mitoxantrone (8 mg/m$^2$) combined with cytarabine for 3 days, and conditionally received carmustine combined with etoposide after bone marrow autotransplantation. Before receiving bone marrow autotransplantation, of the 62 patients (two trials were pooled for statistics and were not individually counted for efficacy), 35 (56%) achieved CR, 10 (16%) achieved PR, and 15 (24%) showed PD. However, the reference did not disclose the efficacy of the two trials individually, and the individual efficacy of trial 2 was not disclosed. Even if it was disclosed, the individual efficacy of the latter could not be shown because of receiving MACOP for 8 weeks at first and then receiving mitoxantrone combined with cytarabine for 3 days.

It has also been reported that all patients received the first-line treatment with anthracyclines and 4 subjects in the second-line treatment received a combination chemotherapy regimen containing mitoxantrone (mitoxantrone+cytarabine+etoposide+prednisone) (High-dose therapy with autologous stem cell transplantation in patients with peripheral T-cell lymphomas, Journal of Bone Marrow Transplantation, A K Blystad et al., 2001, Vol. 27, pp. 711-716). However, the used dosage, period and efficacy evaluation after use of the chemotherapy regimen were not reported. The efficacy of this chemotherapy regimen on peripheral T-cell lymphoma cannot be judged from the reference.

4. Mitoxantrone Liposomes

The liposomal preparation of mitoxantrone used in this patent application is obtained by further optimization of the Chinese patent application 200610102339.8 filed on Dec. 29, 2006 and the PCT application WO2008/080367 A1 filed on Dec. 29, 2007.

In short, as for the treatment of DLBCL and PTCL, the current multi-drug combination therapeutic regimen is not satisfactory in terms of the aspects such as effectiveness and tolerability. There remains an urgent need in the art for a therapeutic agent with improved effectiveness and tolerability.

SUMMARY OF THE INVENTION

The liposomal pharmaceutical preparation according to the present invention has a particle size of about 30-80 nm, and contains a phospholipid with a Tm higher than body temperature in the phospholipid bilayer, so that the phase transition temperature of liposomes is higher than body temperature. Preferably, the phospholipid is phosphatidylcholine, hydrogenated soybean phosphatidylcholine (HSPC), hydrogenated egg yolk phosphatidylcholine, dipalmitoyl phosphatidylcholine (DPPC) or distearoyl phosphatidylcholine (DSPC) or any combination thereof. The normal body temperature of the human body is generally 36-38° C., for example, the typical value is 37° C. Body temperature varies with factors such as age, gender, day and night, mood, and measurement site.

In the liposomal pharmaceutical preparation, the phospholipid with a Tm higher than body temperature in the phospholipid bilayer represent about 50-100 mol/mol %, preferably about 55-95 mol/mol %, more preferably about 60-90 mol/mol % relative to the total phospholipid content.

In the liposomal pharmaceutical preparation, the phospholipid bilayer optionally contains other phospholipids, for example, phospholipids with a Tm value not higher than body temperature, such as dimyristoyl phosphatidylcholine (DMPC) and the like.

The liposomal pharmaceutical preparation optionally contains cholesterol in an amount of 2-60 mol/mol %, such as 5-55 mol/mol %, especially 10-50 mol/mol %, particularly 15-45 mol/mol %, more particularly 20-40 mol/mol % relative to the total moles of each component of the liposomes.

The liposomal pharmaceutical preparation may optionally contain other excipients, for example excipients which further modify the surface characteristics of the liposomes, such as lipid substances modified with hydrophilic polymers, which may be selected, for example, from polyethylene glycol-modified distearoylphosphatidylethanolamine (DSPE-PEG), polyethylene glycol-modified distearoylphosphatidylglycerol (DSPG-PEG), polyethylene glycol-modified cholesterol (chol-PEG), povidone-modified distearoylphosphatidylethanolamine (DSPE-PVP), polyethylene glycol-modified distearoylphosphatidylglycerol (DSPG-PVP) or polyethylene glycol-modified cholesterol (chol-PVP) or combinations thereof, preferably in an amount of 0.1-20 mol/mol %, such as 0.3-18 mol/mol %, 0.5-15 mol/mol %, 0.8-12 mol/mol %, 1-10 mol/mol %, 2-8 mol/mol %, 2.5-7 mol/mol %, or 3-6 mol/mol % and the like relative to phospholipids, on a molar basis.

The liposomal pharmaceutical preparation has a particle size of 35-75 nm, preferably 40-70 nm, especially 40-60 nm.

The liposomal pharmaceutical preparation contains hydrogenated soybean phosphatidylcholine, cholesterol and polyethylene glycol-modified distearoylphosphatidylethanolamine at a mass ratio of 3:1:1, preferably, the polyethylene glycol-modified distearoylphosphatidylethanolamine is polyethylene glycol 2000-modified distearoylphosphatidylethanolamine.

The liposomal pharmaceutical preparation contains an active pharmaceutical ingredient, preferably a multivalent ionic drug.

In the liposomal pharmaceutical preparation, the active pharmaceutical ingredient has two or more dissociable groups with a dissociation constant pKa between 4.5-9.5, preferably between 5.0-9.5, more preferably between 5.5-9.5, particularly preferably between 6.0-9.0, especially between 6.5-9.0.

In the liposomal pharmaceutical preparation, the multivalent ionic drug 15 mitoxantrone.

In the liposomal pharmaceutical preparation, by the total weight of the pharmaceutical preparation, the content of the drug is 0.1-50 wt %, preferably 0.5-40 wt %, more preferably 1-35 wt %, particularly preferably 3-30 wt %, or 5-25 wt %, or 8-20 wt %.

The liposomal pharmaceutical preparation optionally contains one or more other pharmaceutical ingredients, and/or pharmaceutically acceptable carriers and/or excipients.

In the liposomal pharmaceutical preparation, the liposomes contain a counter ion, preferably a multivalent counter ion, for example an organic acid radical, such as the radical of a saturated or unsaturated organic acid selected from: citric acid, tartaric acid, fumaric acid, oxalic acid, malonic acid, succinic acid, malic acid, maleic acid, etc., inorganic acid radical such as sulfate, phosphate or ionized form of amino acid, such as cystine, preferably citrate, sulfate or phosphate.

In the liposomal pharmaceutical preparation, the multivalent counter ion has two or more charges opposite to that of the active pharmaceutical ingredient.

In the liposomal pharmaceutical preparation, the liposomes contain phosphatidylcholine, hydrogenated soybean phosphatidylcholine, hydrogenated egg yolk phosphatidylcholine, dipalmitoyl phosphatidylcholine or distearoyl phosphatidylcholine or combination thereof.

A method of preparing the liposomal pharmaceutical preparation may comprise the steps of: (1) preparing the liposomes from a phospholipid with a Tm higher than body temperature and optionally other phospholipids and/or cholesterol; and (2) encapsulating the drug of interest, particularly a multivalent ionic drug, within the liposome.

In the first aspect, the present invention provides a liposomal pharmaceutical preparation comprising mitoxantrone liposomes having a particle size of about 30-80 nm and comprising mitoxantrone as an active ingredient, wherein mitoxantrone and the multivalent counter ion within the liposomes form a poorly soluble precipitate, the phospholipid bilayer of the liposomes comprises a phospholipid with a phase transition temperature (Tm) higher than body temperature, so that the phase transition temperature of liposomes is higher than the body temperature.

Preferably, in the above-mentioned liposomal pharmaceutical preparation, the phospholipid with a Tm higher than body temperature is selected from phosphatidylcholine, hydrogenated soybean phosphatidylcholine, hydrogenated egg yolk phosphatidylcholine, dipalmitoyl phosphatidylcholine, distearoyl phosphatidylcholine and any combination thereof; and/or the liposomes have a particle size of about 35-75 nm, preferably 40-70 nm, further preferably 40-60 nm, particularly preferably 60 nm.

Preferably, in the above-mentioned liposomal pharmaceutical preparation, the phospholipid bilayer contains hydrogenated soybean phosphatidylcholine, cholesterol, and polyethylene glycol 2000-modified distearoylphosphatidylethanolamine at a mass ratio of 3:1:1, and/or the liposomes have a particle size of about 60 nm, and the counter ion is sulfate ion.

In the second aspect, the present invention provides use of the above-mentioned liposomal pharmaceutical preparation in the preparation of a medicament for treating lymphoma, wherein the lymphoma is preferably non-Hodgkin's lymphoma, further preferably aggressive non-Hodgkin's lymphoma, more preferably diffuse large B-cell lymphoma or peripheral T-cell lymphoma, and more further preferably relapsed or refractory diffuse large B-cell lymphoma or peripheral T-cell lymphoma.

The present invention provides use of the above-mentioned liposomal pharmaceutical preparation in the preparation of a medicament for treating lymphoma, wherein the liposomal pharmaceutical preparation is used as a single anti-tumor therapeutic agent and is not combined with other anti-tumor agents.

The present invention provides use of the above-mentioned liposomal pharmaceutical preparation in the preparation of a medicament for treating lymphoma, wherein the liposomal pharmaceutical preparation is used for second-line and subsequent treatment of the lymphoma, preferably for third-line and subsequent treatment of diffuse large B-cell lymphoma, and for second-line and subsequent treatment of peripheral T-cell lymphoma.

The present invention provides use of the above-mentioned liposomal pharmaceutical preparation in the preparation of a medicament for treating lymphoma, wherein the administration frequency of the liposomal pharmaceutical preparation is once per 1-4 weeks, preferably once per 3-4 weeks, and further preferably once per 4 weeks.

The present invention provides use of the above-mentioned liposomal pharmaceutical preparation in the preparation of a medicament for treating lymphoma, wherein the administration dosage of the liposomal pharmaceutical preparation is 6-30 mg/m$^2$, preferably 14-24 mg/m$^2$.

The present invention provides use of the above-mentioned liposomal pharmaceutical preparation in the preparation of a medicament for treating lymphoma, wherein the administration period of the liposomal pharmaceutical preparation via drip is 30 min-120 min, preferably 60 min-120 min, further preferably not less than 60 min, more preferably 60±5 min.

The present invention provides the use of the above-mentioned liposomal pharmaceutical preparation in the preparation of a medicament for treating lymphoma, wherein the total administration dosage of the liposomal pharmaceutical preparation administered to each patient is not more than 200 mg/m$^2$, preferably not more than 160 mg/m$^2$, and further preferably not more than 140 mg/m$^2$.

In a third aspect, the present invention provides a method for treating lymphoma with the above-mentioned liposomal pharmaceutical preparation, comprising administering to a subject in need thereof a liposomal pharmaceutical preparation of mitoxantrone, wherein the lymphoma is preferably non-Hodgkin's lymphoma, further preferably aggressive non-Hodgkin's lymphoma, more preferably diffuse large B-cell lymphoma or peripheral T-cell lymphoma, more further preferably relapsed or refractory diffuse large B-cell lymphoma or peripheral T-cell lymphoma.

According to the above-mentioned method for treating lymphoma, wherein the liposomal pharmaceutical preparation of mitoxantrone is administered as a single anti-tumor therapeutic agent without being combined with other anti-tumor agents.

According to the above-mentioned method for treating lymphoma, wherein the subject at least has received a first-line treatment. For example, the subject has diffuse large B-cell lymphoma and at least has received a first-line and/or second-line treatment, or for example the subject has peripheral T-cell lymphoma and at least has received a first-line treatment.

According to the above-mentioned method for treating lymphoma, wherein the liposomal pharmaceutical preparation is administered once per 1, 2, 3, 4, 5, 6, 7 or 8 weeks, preferably once per 3-6 weeks, and further preferably once per 4 weeks; and/or the liposomal pharmaceutical preparation of mitoxantrone is administered to the subject 1, 2, 3, 4, 5 or 6 times, for example 2, 3, 4 or 5 times.

According to the above-mentioned method for treating lymphoma, wherein the administration dosage of the liposomal pharmaceutical preparation is 6-30 mg/m$^2$, such as 8, 10, 12, 14, 16, 18, 20, 22, 24, 26, 28 or 30 mg/m$^2$, preferably 14-24 mg/m$^2$.

According to the above-mentioned method for treating lymphoma, wherein the liposomal pharmaceutical preparation is administered to the subject by intravenous drip, and the administration period via drip is not less than 30, 40, 45, 50, 60, 70, 75, 80, 90, 100, 110 or 120 min, between 30 min and 120 min, preferably between 40 min and 80 min, between 60 min and 120 min, further preferably not less than 60 min, more preferably 60 min.

According to the above-mentioned method for treating lymphoma, wherein the total dosage of the liposomal pharmaceutical preparation administered to each subject (patient) is not more than 200 mg/m$^2$, preferably not more than 160 mg/m$^2$, and further preferably not more than 140 mg/m$^2$.

According to the above-mentioned method for treating lymphoma, wherein the route of administration can be selected from oral administration, injection administration and local administration, preferably injection administration; further, injection administration can be selected from intravenous injection, subcutaneous injection, intramuscular injection, preferably intravenous injection; further, intravenous injection can be selected from intravenous drip and intravenous bolus injection, preferably intravenous drip.

According to the above-mentioned method for treating lymphoma, wherein the route of administration is intravenous drip. The method comprises diluting the liposomes in sodium chloride injection or glucose injection, preferably in glucose injection; and then administrating to the subject; wherein the concentration of the sodium chloride injection is 0.5%-1%, preferably 0.9%; the concentration of the glucose injection is 1%-10%, preferably 5%.

According to the above-mentioned method for treating lymphoma, it comprises formulating the liposomal drug into a solution that can be directly infused before administering to the subject, wherein the concentration of the formulated solution of liposomes that can be directly infused is 0.05 mg/ml-0.5 mg/ml, preferably 0.08 mg/ml-0.4 mg/ml, more preferably 0.1 mg/ml-0.3 mg/ml, more preferably 0.1 mg/ml, 0.15 mg/ml, 0.2 mg/ml, 0.25 mg/ml or 0.3 mg/ml.

According to the above-mentioned method for treating lymphoma, after 3 or more cycles of treatment (each cycle means that the liposomal drug formulation is administered once), a higher overall remission rate (ORR) than that with the HDAC inhibitor used alone can be achieved.

According to the above-mentioned method for treating lymphoma, after 3 or more cycles of treatment, the overall remission rate (ORR) of the method is at least 30%, preferably at least 40%; further, the overall remission rate is 30%-60%.

Among them, the patient has previously experienced one, two or more treatments selected from: CHOP (cyclophosphamide+doxorubicin+vincristine+prednisone), DICE (dexamethasone+ifosfamide+carboplatin+etoposide), Gemox (gemcitabine+oxaliplatin), R-CHOP (rituximab-cyclophosphamide+doxorubicin+vincristine+prednisone), EP (etoposide+cisplatin), etoposide, R-CHOP+ibrutinib (rituximab-cyclophosphamide+doxorubicin+vincristine+prednisone+ibrutinib), ICE (ifosfamide+carboplatin+etoposide), R-EPOCH (rituximab-etoposide+vincristine+pirarubicin+cyclophosphamide+prednisone), FC (fluorouracil+carboplatin), GCP (gemcitabine+cyclophosphamide+dexamethasone), CHOP+Mesna (cyclophosphamide+doxorubicin+vincristine+prednisone+mesna), R-MTX (rituximab-methotrexate), GEMOX+TNF (gemcitabine+oxaliplatin+human tumor necrosis factor), ECOP (etoposide, cyclophosphamide, vincristine, prednisone), CTP (cyclophosphamide+thalidomide+prednisone), EPP (etoposide+cisplatin+dexamethasone), OB (bleomycin+vincristine), ABVD (adriamycin, bleomycin, vinblastine, dacarbazine), CDOP (cyclophosphamide+doxorubicin liposome+vincristine+prednisone), GDP (gemcitabine+cisplatin+dexamethasone), DICE+Chidamide (dexamethasone+ifosfamide+carboplatin+etoposide+chidamide), R-DA-EPOCH (rituximab-daunorubicin+cytarabine-etoposide+vincristine+pirarubicin+cyclophosphamide+prednisone), GDE (gemcitabine+ cisplatin+etoposide), R-GDP (rituximab-gemcitabine+cisplatin+dexamethasone), R (rituximab), R-GDE (rituximab-gemcitabine+cisplatin+etoposide).

In one aspect, the present invention provides a liposomal pharmaceutical preparation comprising mitoxantrone liposomes containing mitoxantrone as an active ingredient, and wherein mitoxantrone and the multivalent counter ion within the liposomes form a poorly soluble precipitate. The phospholipid bilayer of the liposomes comprises a phospholipid with a phase transition temperature (Tm) higher than body temperature, so that the phase transition temperature of liposomes is higher than the body temperature.

In one embodiment, the liposomes have a particle size of about 30-80 nm, for example about 35-75 nm, preferably 40-70 nm, further preferably 40-60 nm, particularly preferably 60 mu.

In another embodiment, the phospholipid with a Tm higher than body temperature is selected from phosphatidylcholine, hydrogenated soybean phosphatidylcholine, hydrogenated egg yolk phosphatidylcholine, dipalmitoyl phosphatidylcholine, distearoyl phosphatidylcholine and any combination thereof.

In another embodiment, the phospholipid bilayer contains hydrogenated soybean phosphatidylcholine, cholesterol and polyethylene glycol 2000-modified distearoylphosphatidylethanolamine at a mass ratio of 3:1:1, and the counter ion is sulfate ion.

In another aspect, the present invention provides a method for treating lymphoma comprising administering a liposomal pharmaceutical preparation of mitoxantrone, such as the liposomal pharmaceutical preparation described in the above aspect according to the present invention to a subject in need thereof.

Preferably, the lymphoma is non-Hodgkin's lymphoma, further preferably aggressive non-Hodgkin's lymphoma, more preferably diffuse large B-cell lymphoma or peripheral T-cell lymphoma, more further preferably relapsed or refractory diffuse large B-cell lymphoma or peripheral T-cell lymphoma, for example, the peripheral T-cell lymphoma is selected from non-specific peripheral T-cell lymphoma, angioimmunoblastic T-cell lymphoma, ALK+ systemic anaplastic large T-cell lymphoma, ALK− systemic anaplastic large T-cell lymphoma, extranodal NK/T-cell lymphoma, nasal-type, enteropathy-associated T-cell lymphoma, primary hepatosplenic γδ T-cell lymphoma and subcutaneous panniculitis-like T-cell lymphoma.

In one embodiment, the administration means that the liposomal pharmaceutical preparation of mitoxantrone is administered as a single anti-tumor therapeutic agent without being combined with other anti-tumor agents.

In another embodiment, the subject at least has received a first-line treatment. For example, the subject has diffuse large B-cell lymphoma and at least has received a first-line and/or second-line treatment, or for example the subject has peripheral T-cell lymphoma and at least has received a first-line treatment.

In still another embodiment, the patient has previously experienced one, two or more treatments selected from: CHOP (cyclophosphamide+doxorubicin+vincristine+prednisone), DICE (dexamethasone+ifosfamide+carboplatin+etoposide), Gemox (gemcitabine oxaliplatin), R-CHOP (rituximab-cyclophosphamide+doxorubicin+vincristine+prednisone), EP (etoposide cisplatin), etoposide, R-CHOP ibrutinib (rituximab-cyclophosphamide+doxorubicin+vincristine+prednisone+ibrutinib), ICE (ifosfamide+carboplatin+etoposide), R-EPOCH (rituximab-etoposide+vincristine+pirarubicin+cyclophosphamide+prednisone), FC (fluorouracil+carboplatin), GCP (gemcitabine+cyclophosphamide+dexamethasone), CHOP+Mesna (cyclophosphamide+doxorubicin+vincristine+prednisone+mesna), R-MTX (rituximab-methotrexate), GEMOX+TNF (gemcitabine+oxaliplatin+human tumor necrosis factor), ECOP (etoposide, cyclophosphamide, vincristine, prednisone), CTP (cyclophosphamide+thalidomide+prednisone), EPP (etoposide+cisplatin+dexamethasone), OB (bleomycin+vincristine), ABVD (adriamycin, bleomycin, vinblastine, dacarbazine), CDOP (cyclophosphamide+doxorubicin liposome+vincristine+prednisone), GDP (gemcitabine+cisplatin+dexamethasone), DICE+Chidamide (dexamethasone+ifosfamide+carboplatin+etoposide+chidamide), R-DA-EPOCH (rituximab-daunorubicin+cytarabine-etoposide+vincristine+pirarubicin+cyclophosphamide+prednisone), GDE (gemcitabine+cisplatin+etoposide), R-GDP (rituximab-gemcitabine+cisplatin+dexamethasone), R (rituximab) and R-GDE (rituximab-gemcitabine+cisplatin+etoposide).

In the treatment method according to the present invention, for example, the treatment can be performed as follows:

the liposomal pharmaceutical preparation of mitoxantrone is administered once per 1, 2, 3, 4, 5, 6, 7 or 8 weeks, preferably once per 3-6 weeks, and further preferably once per 4 weeks; and/or the liposomal pharmaceutical preparation of mitoxantrone is administered to the subject 1, 2, 3, 4, 5 or 6 times, for example 2, 3, 4 or 5 times; and/or the liposomal pharmaceutical preparation of mitoxantrone is administered to the subject at a dosage of 6-30 mg/m$^2$, such as 8, 10, 12, 14, 16, 18, 20, 22, 24, 26, 28 or 30 mg/m$^2$, preferably 14-24 mg/m$^2$.

In one embodiment, the liposomal pharmaceutical preparation of mitoxantrone is administered to the subject via intravenous drip, and the drip period is not less than 30, 40, 45, 50, 60, 70, 75, 80, 90, 100, 110 or 120 min, preferably 40-80 min, more preferably about 60 min.

In another embodiment, the total dosage of the liposomal pharmaceutical preparation administered to the subject is not more than 200 mg/m$^2$, for example not more than 120, 140, 160, 180 or 200 mg/m$^2$, preferably not more than 160 mg/m$^2$, and further preferably not more than 140 mg/m$^2$.

In one embodiment, the treatment method according to the present invention comprises administering to the subject the liposomal pharmaceutical preparation of mitoxantrone 3 or more times for treatment, and the method achieves a higher overall remission rate (ORR) than the HDAC inhibitor used alone.

In one embodiment, the treatment method according to the present invention comprises administering to the subject the liposomal pharmaceutical preparation of mitoxantrone 3 or more times for treatment, and the overall remission rate (ORR) of the method is at least 30%, preferably at least 40%; further, the overall remission rate is 30%-60%.

EXAMPLES

Example 1 Preparation of Mitoxantrone Liposomes

HSPC, Chol and DSPE-PEG2000 were weighed at a mass ratio of 3:1:1 and dissolved in 95% ethanol to obtain a clear solution. The ethanol solution of phospholipids was mixed with 300 mM ammonium sulfate solution, shaken and hydrated for 1 h at 60-65° C. to obtain heterogeneous multilamellar liposomes. Then a Microfluidizer was used to reduce the particle size of liposomes. The obtained sample was diluted 200 times with a 0.9% NaCl solution, and then detected with NanoZS. The average particle size of the particles was about 60 nm, and the main peak was between 40 nm and 60 nm. Afterwards, an ultrafiltration device was used to remove the ammonium sulfate in the outer phase of the blank liposomes, and the outer phase was replaced with 290 mM sucrose and 10 mM glycine to form a transmembrane ammonium sulfate gradient. Mitoxantrone hydrochloride solution (10 mg/mL) was added to the blank liposomes at a lipid:drug ratio of 16:1, and the drug was loaded at 60-65° C. After incubating for about 1 h, gel exclusion chromatography was used to prove that the encapsulation efficiency was about 100%. The weight ratio of HSPC:Chol:DSPE-PEG2000:mitoxantrone was 9.58:3.19:3.19:1, and the osmotic pressure of the sucrose-glycine solution was close to the physiological value.

Example 2 Investigation on the Stability of Mitoxantrone Liposomes

The mitoxantrone liposomes prepared by the above-mentioned method were prepared into two samples at the concentration of 0.1 mg/ml and 0.2 mg/ml by using 5% glucose injection and 0.9% sodium chloride injection (normal saline) as diluents and using glass infusion bottles as containers, respectively. The parameters such as pH of the solution, average particle size of liposomes, concentration of encapsulated drug, phospholipids, lysolecithin, related substances, and content were examined at 30° C., at 30° C. in the dark and under refrigerated condition at 2-8° C. at six time points of 0 h, 2 h, 4 h, 6 h, 8 h and 24 h, respectively. The experimental results are shown in Table 1-4 below.

TABLE 1

Stability of mitoxantrone liposomes diluted with 5% glucose injection, glass infusion bottle, 0.1 mg/mL

| Condition | Time point (h) | pH | Average particle size (nm) | Concentration of encapsulated drug (mg/mL) | Phospholipids (mg/mL) Cholesterol | $HSPC_{C16-18}$ | $HSPC_{C18-18}$ | Lysolecithin (mg/mL) | Mitoxantrone peak purity | Related substance (%) Maximum single impurity | Content (mg/mL) |
|---|---|---|---|---|---|---|---|---|---|---|---|
| 30° C. | 0 | 6.47 | 63.1 | 0.085 | 0.279 | 0.192 | 0.669 | not detected | 99.82 | 0.06 | 0.091 |
| | 2 | 6.45 | 63.6 | 0.087 | 0.286 | 0.197 | 0.678 | ND | 99.85 | 0.05 | 0.091 |
| | 4 | 6.46 | 63.3 | 0.087 | 0.289 | 0.199 | 0.671 | ND | 99.86 | 0.06 | 0.090 |
| | 6 | 6.46 | 63.4 | 0.086 | 0.289 | 0.199 | 0.670 | ND | 99.89 | 0.04 | 0.089 |
| | 8 | 6.47 | 63.5 | 0.086 | 0.291 | 0.200 | 0.674 | ND | 99.90 | 0.04 | 0.093 |
| | 24 | 6.48 | 63.5 | 0.088 | 0.287 | 0.191 | 0.661 | not detected | 99.94 | 0.03 | 0.090 |
| | Average value | 6.5 | 63 | 0.087 | 0.287 | 0.196 | 0.670 | N/A | 99.88 | 0.05 | 0.091 |
| | RSD (%) | 0.2 | 0.3 | 1.1 | 1.4 | 2.0 | 0.8 | N/A | 0.1 | 26.8 | 1.3 |
| 30° C. in the dark | 0 | 6.46 | 62.9 | 0.086 | 0.286 | 0.197 | 0.669 | not detected | 99.87 | 0.05 | 0.091 |
| | 2 | 6.47 | 63.4 | 0.087 | 0.289 | 0.193 | 0.675 | ND | 99.88 | 0.05 | 0.091 |
| | 4 | 6.47 | 63.9 | 0.086 | 0.292 | 0.200 | 0.686 | ND | 99.89 | 0.04 | 0.091 |
| | 6 | 6.45 | 62.9 | 0.088 | 0.288 | 0.197 | 0.665 | ND | 99.90 | 0.04 | 0.092 |
| | 8 | 6.46 | 63.6 | 0.086 | 0.288 | 0.200 | 0.678 | ND | 99.87 | 0.05 | 0.091 |
| | 24 | 6.46 | 64.0 | 0.088 | 0.283 | 0.194 | 0.675 | not detected | 99.94 | 0.03 | 0.091 |
| | Average value | 6.5 | 63 | 0.087 | 0.288 | 0.197 | 0.675 | N/A | 99.89 | 0.04 | 0.091 |
| | RSD (%) | 0.1 | 0.7 | 1.3 | 1.0 | 1.5 | 1.1 | N/A | 0.1 | 19.6 | 0.5 |
| Refrigerated at 2-8° C. | 0 | 6.46 | 63.8 | 0.084 | 0.287 | 0.192 | 0.687 | not detected | 99.66 | 0.06 | 0.091 |
| | 2 | 6.47 | 62.9 | 0.088 | 0.291 | 0.192 | 0.683 | ND | 99.81 | 0.06 | 0.091 |
| | 4 | 6.47 | 63.4 | 0.087 | 0.287 | 0.195 | 0.672 | ND | 99.81 | 0.06 | 0.091 |
| | 6 | 6.47 | 63.7 | 0.088 | 0.297 | 0.198 | 0.682 | ND | 99.76 | 0.07 | 0.091 |
| | 8 | 6.46 | 62.8 | 0.087 | 0.282 | 0.187 | 0.681 | ND | 99.77 | 0.07 | 0.092 |
| | 24 | 6.46 | 63.6 | 0.087 | 0.283 | 0.193 | 0.686 | not detected | 99.84 | 0.06 | 0.090 |
| | Average value | 6.5 | 63 | 0.087 | 0.288 | 0.193 | 0.682 | N/A | 99.77 | 0.06 | 0.091 |
| | RSD (%) | 0.1 | 0.7 | 1.7 | 1.8 | 2.0 | 0.8 | N/A | 0.1 | 8.2 | 0.8 |

N/A: Not applicable; ND: Not detected

TABLE 2

Stability of mitoxantrone liposomes diluted with 0.9% sodium chloride injection, glass infusion bottle, 0.1 mg/mL

| Condition | Time point (h) | pH | Average particle size (nm) | Concentration of encapsulated drug (mg/mL) | Phospholipids (mg/mL) | | | Lysolecithin (mg/mL) | Related substance (%) | | Content (mg/mL) |
|---|---|---|---|---|---|---|---|---|---|---|---|
| | | | | | Cholesterol | $HSPC_{C16-18}$ | $HSPC_{C18-18}$ | | Mitoxantrone peak purity | Maximum single impurity | |
| 30° C. | 0 | 6.56 | 62.0 | 0.088 | 0.284 | 0.196 | 0.694 | not detected | 99.82 | 0.11 | 0.093 |
| | 2 | 6.57 | 62.3 | 0.088 | 0.287 | 0.195 | 0.711 | ND | 99.80 | 0.10 | 0.093 |
| | 4 | 6.56 | 63.4 | 0.087 | 0.291 | 0.198 | 0.703 | ND | 99.84 | 0.11 | 0.094 |
| | 6 | 6.58 | 63.8 | 0.088 | 0.287 | 0.192 | 0.713 | ND | 99.85 | 0.11 | 0.094 |
| | 8 | 6.57 | 63.2 | 0.088 | 0.289 | 0.201 | 0.697 | ND | 99.82 | 0.11 | 0.093 |
| | 24 | 6.55 | 65.4 | 0.089 | 0.287 | 0.201 | 0.693 | not detected | 99.84 | 0.10 | 0.093 |
| | Average value | 6.6 | 63 | 0.088 | 0.288 | 0.197 | 0.702 | N/A | 99.83 | 0.11 | 0.093 |
| | RSD (%) | 0.2 | 1.9 | 0.7 | 0.9 | 1.7 | 1.2 | N/A | 0.1 | 4.2 | 0.7 |
| 30° C. in the dark | 0 | 6.58 | 61.9 | 0.088 | 0.282 | 0.197 | 0.681 | not detected | 99.84 | 0.06 | 0.094 |
| | 2 | 6.56 | 62.1 | 0.087 | 0.282 | 0.200 | 0.694 | ND | 99.85 | 0.06 | 0.094 |
| | 4 | 6.56 | 63.5 | 0.089 | 0.288 | 0.190 | 0.702 | ND | 99.82 | 0.07 | 0.093 |
| | 6 | 6.59 | 63.4 | 0.088 | 0.289 | 0.194 | 0.701 | ND | 99.85 | 0.06 | 0.094 |
| | 8 | 6.57 | 64.3 | 0.088 | 0.283 | 0.192 | 0.688 | ND | 99.79 | 0.10 | 0.093 |
| | 24 | 6.58 | 66.1 | 0.088 | 0.290 | 0.196 | 0.700 | not detected | 99.81 | 0.09 | 0.094 |
| | Average value | 6.6 | 64 | 0.088 | 0.286 | 0.195 | 0.694 | N/A | 99.83 | 0.07 | 0.093 |
| | RSD (%) | 0.2 | 2.4 | 0.7 | 1.3 | 1.8 | 1.2 | N/A | 0.1 | 24.2 | 0.7 |
| Refrigerated at 2-8° C. | 0 | 6.59 | 61.6 | 0.089 | 0.280 | 0.195 | 0.694 | not detected | 99.83 | 0.06 | 0.093 |
| | 2 | 6.61 | 62.7 | 0.089 | 0.288 | 0.204 | 0.717 | ND | 99.82 | 0.07 | 0.095 |
| | 4 | 6.58 | 62.9 | 0.087 | 0.283 | 0.198 | 0.702 | ND | 99.82 | 0.07 | 0.094 |
| | 6 | 6.58 | 63.9 | 0.088 | 0.283 | 0.198 | 0.690 | ND | 99.83 | 0.08 | 0.093 |
| | 8 | 6.61 | 64.0 | 0.088 | 0.283 | 0.196 | 0.684 | ND | 99.76 | 0.12 | 0.093 |
| | 24 | 6.59 | 63.0 | 0.088 | 0.284 | 0.194 | 0.680 | not | 99.82 | 0.08 | 0.093 |
| | Average value | 6.6 | 63 | 0.088 | 0.284 | 0.198 | 0.694 | N/A | 99.81 | 0.08 | 0.093 |
| | RSD (%) | 0.2 | 1.4 | 0.8 | 0.9 | 1.8 | 1.9 | N/A | 0.1 | 24.1 | 0.8 |

N/A: Not applicable; ND: Not detected

TABLE 3

Stability of mitoxantrone liposomes diluted with 5% glucose injection, glass infusion bottle, 0.2 mg/mL

| Condition | Time point (h) | pH | Average particle size (nm) | Concentration of encapsulated drug (mg/mL) | Phospholipids (mg/mL) | | | Lysolecithin (mg/mL) | Related substance (%) | | Content (mg/mL) |
|---|---|---|---|---|---|---|---|---|---|---|---|
| | | | | | Cholesterol | $HSPC_{C16-18}$ | $HSPC_{C18-18}$ | | Mitoxantrone peak purity | Maximum single impurity | |
| 30° C. | 0 | 6.57 | 63.0 | 0.182 | 0.601 | 0.404 | 1.445 | not detected | 99.87 | 0.10 | 0.186 |
| | 2 | 6.57 | 63.0 | 0.181 | 0.603 | 0.396 | 1.411 | ND | 99.86 | 0.10 | 0.189 |
| | 4 | 6.56 | 63.1 | 0.179 | 0.595 | 0.395 | 1.374 | ND | 99.85 | 0.11 | 0.189 |
| | 6 | 6.59 | 63.2 | 0.183 | 0.586 | 0.404 | 1.404 | ND | 99.85 | 0.10 | 0.188 |
| | 8 | 6.59 | 63.1 | 0.182 | 0.592 | 0.397 | 1.388 | ND | 99.85 | 0.11 | 0.188 |
| | 24 | 6.58 | 64.0 | 0.179 | 0.581 | 0.401 | 1.371 | not detected | 99.86 | 0.10 | 0.186 |
| | Average value | 6.6 | 63 | 0.181 | 0.593 | 0.399 | 1.399 | N/A | 99.86 | 0.10 | 0.188 |
| | RSD (%) | 0.2 | 0.6 | 1.0 | 1.4 | 1.0 | 2.0 | N/A | 0.1 | 4.9 | 0.7 |

TABLE 3-continued

Stability of mitoxantrone liposomes diluted with 5% glucose injection, glass infusion bottle, 0.2 mg/mL

| Condition | Time point (h) | pH | Average particle size (nm) | Concentration of encapsulated drug (mg/mL) | Phospholipids (mg/mL) | | | Lysolecithin (mg/mL) | Related substance (%) | | Content (mg/mL) |
|---|---|---|---|---|---|---|---|---|---|---|---|
| | | | | | Cholesterol | HSPC$_{C16-18}$ | HSPC$_{C18-18}$ | | Mitoxantrone peak purity | Maximum single impurity | |
| 30° C. in the dark | 0 | 6.55 | 63.3 | 0.179 | 0.605 | 0.398 | 1.405 | not detected | 99.85 | 0.10 | 0.186 |
| | 2 | 6.56 | 63.6 | 0.180 | 0.589 | 0.400 | 1.392 | ND | 99.82 | 0.11 | 0.186 |
| | 4 | 6.56 | 63.0 | 0.181 | 0.591 | 0.392 | 1.396 | ND | 99.87 | 0.09 | 0.185 |
| | 6 | 6.57 | 62.7 | 0.181 | 0.599 | 0.381 | 1.387 | ND | 99.84 | 0.11 | 0.185 |
| | 8 | 6.57 | 63.4 | 0.181 | 0.595 | 0.393 | 1.414 | ND | 99.83 | 0.11 | 0.187 |
| | 24 | 6.56 | 63.3 | 0.179 | 0.579 | 0.398 | 1.347 | not detected | 99.84 | 0.11 | 0.186 |
| | Average value | 6.6 | 63 | 0.180 | 0.593 | 0.393 | 1.390 | N/A | 99.84 | 0.10 | 0.186 |
| | RSD (%) | 0.1 | 0.5 | 0.5 | 1.5 | 1.8 | 1.6 | N/A | 0.1 | 6.9 | 0.4 |
| Refrigerated at 2-8° C. | 0 | 6.56 | 63.5 | 0.182 | 0.589 | 0.407 | 1.394 | not detected | 99.85 | 0.10 | 0.188 |
| | 2 | 6.56 | 62.8 | 0.181 | 0.594 | 0.398 | 1.386 | ND | 99.85 | 0.10 | 0.190 |
| | 4 | 6.55 | 62.8 | 0.180 | 0.598 | 0.395 | 1.417 | ND | 99.84 | 0.11 | 0.189 |
| | 6 | 6.57 | 63.1 | 0.182 | 0.580 | 0.396 | 1.388 | ND | 99.85 | 0.10 | 0.189 |
| | 8 | 6.56 | 63.6 | 0.180 | 0.585 | 0.389 | 1.395 | ND | 99.78 | 0.11 | 0.188 |
| | 24 | 6.56 | 63.2 | 0.174 | 0.580 | 0.387 | 1.375 | not detected | 99.80 | 0.10 | 0.185 |
| | Average value | 6.6 | 63 | 0.180 | 0.588 | 0.395 | 1.392 | N/A | 99.83 | 0.10 | 0.188 |
| | RSD (%) | 0.1 | 0.5 | 1.7 | 1.2 | 1.8 | 1.0 | N/A | 0.1 | 2.3 | 0.9 |

N/A: Not applicable; ND: Not detected

TABLE 4

Stability of mitoxantrone liposomes diluted with 0.9% sodium chloride injection, glass infusion bottle, 0.2 mg/mL

| Condition | Time point (h) | pH | Average particle size (nm) | Concentration of encapsulated drug (mg/mL) | Phospholipids (mg/mL) | | | Lysolecithin (mg/mL) | Related substance (%) | | Content (mg/mL) |
|---|---|---|---|---|---|---|---|---|---|---|---|
| | | | | | Cholesterol | HSPC$_{C16-18}$ | HSPC$_{C18-18}$ | | Mitoxantrone peak purity | Maximum single impurity | |
| 30° C. | 0 | 6.58 | 61.8 | 0.183 | 0.568 | 0.407 | 1.394 | not detected | 99.80 | 0.06 | 0.189 |
| | 2 | 6.57 | 63.1 | 0.182 | 0.574 | 0.411 | 1.401 | ND | 99.85 | 0.06 | 0.188 |
| | 4 | 6.57 | 62.9 | 0.178 | 0.569 | 0.404 | 1.391 | ND | 99.80 | 0.08 | 0.190 |
| | 6 | 6.59 | 62.6 | 0.182 | 0.569 | 0.405 | 1.385 | ND | 99.78 | 0.12 | 0.191 |
| | 8 | 6.57 | 63.3 | 0.182 | 0.574 | 0.412 | 1.377 | ND | 99.87 | 0.08 | 0.189 |
| | 24 | 6.57 | 65.3 | 0.179 | 0.577 | 0.392 | 1.419 | not detected | 99.81 | 0.08 | 0.191 |
| | Average value | 6.6 | 63 | 0.181 | 0.572 | 0.405 | 1.395 | N/A | 99.82 | 0.08 | 0.190 |
| | RSD (%) | 0.1 | 1.9 | 1.0 | 0.6 | 1.8 | 1.0 | N/A | 0.1 | 29.9 | 0.6 |
| 30° C. in the dark | 0 | 6.59 | 62.5 | 0.178 | 0.564 | 0.409 | 1.385 | not detected | 99.85 | 0.10 | 0.185 |
| | 2 | 6.58 | 63.4 | 0.180 | 0.568 | 0.401 | 1.382 | ND | 99.84 | 0.11 | 0.186 |
| | 4 | 6.56 | 63.3 | 0.181 | 0.570 | 0.404 | 1.435 | ND | 99.84 | 0.11 | 0.188 |
| | 6 | 6.55 | 63.2 | 0.172 | 0.572 | 0.411 | 1.404 | ND | 99.83 | 0.11 | 0.186 |
| | 8 | 6.57 | 63.3 | 0.173 | 0.570 | 0.402 | 1.383 | ND | 99.83 | 0.11 | 0.189 |
| | 24 | 6.58 | 65.9 | 0.175 | 0.579 | 0.400 | 1.393 | not detected | 99.81 | 0.11 | 0.189 |
| | Average value | 6.6 | 64 | 0.176 | 0.571 | 0.404 | 1.397 | N/A | 99.83 | 0.11 | 0.187 |
| | RSD (%) | 0.2 | 1.8 | 1.9 | 0.9 | 1.1 | 1.4 | N/A | 0.1 | 2.5 | 0.8 |

TABLE 4-continued

Stability of mitoxantrone liposomes diluted with 0.9% sodium chloride injection, glass infusion bottle, 0.2 mg/mL

| Con-dition | Time point (h) | pH | Average particle size (nm) | Concentration of encapsulated drug (mg/mL) | Phospholipids (mg/mL) Cholesterol | HSPC$_{C16-18}$ | HSPC$_{C18-18}$ | Lysolecithin (mg/mL) | Related substance (%) Mitoxantrone peak purity | Maximum single impurity | Content (mg/mL) |
|---|---|---|---|---|---|---|---|---|---|---|---|
| Refrigerated at 2-8° C. | 0 | 6.55 | 62.9 | 0.183 | 0.579 | 0.408 | 1.386 | not detected | 99.85 | 0.06 | 0.186 |
|  | 2 | 6.54 | 62.1 | 0.181 | 0.574 | 0.421 | 1.404 | ND | 99.89 | 0.06 | 0.188 |
|  | 4 | 6.59 | 62.3 | 0.180 | 0.578 | 0.406 | 1.425 | ND | 99.79 | 0.11 | 0.192 |
|  | 6 | 6.57 | 62.0 | 0.182 | 0.574 | 0.405 | 1.399 | ND | 99.83 | 0.11 | 0.190 |
|  | 8 | 6.58 | 64.6 | 0.179 | 0.573 | 0.401 | 1.418 | ND | 99.75 | 0.19 | 0.189 |
|  | 24 | 6..56 | 62.5 | 0.179 | 0.588 | 0.400 | 1.416 | not detected | 99.84 | 0.06 | 0.190 |
| Average value | | 6.6 | 63 | 0.181 | 0.578 | 0.407 | 1.408 | N/A | 99.82 | 0.10 | 0.189 |
| RSD (%) | | 0.3 | 1.6 | 0.9 | 1.0 | 1.9 | 1.0 | N/A | 0.1 | 54.0 | 0.9 |

N/A: Not applicable; ND: Not detected

The above results show that, under the same concentration and the same storage condition, by using glucose injection and sodium chloride injection as diluents, the parameters such as pH of the obtained solutions, concentration of encapsulated drug, phospholipids, lysolecithin, related substances, and content over time are not significantly different, while the average particle sizes of mitoxantrone liposomes are significantly different. When 0.9% sodium chloride injection is used as the diluent, the average particle size of mitoxantrone liposomes from 0 h to 24 h has an obvious increasing trend, but when 0.5% glucose injection is used as the diluent, the average particle size of the liposomal drug from 0 h to 24 h has little change.

In addition, under the same diluent and the same storage condition, there are no significant differences in parameters of mitoxantrone liposomes with the drug concentrations of 0.1 mg/ml and 0.2 mg/ml, such as pH of the solutions, average particle size, concentration of encapsulated drug, phospholipids, lysolecithin, related substances, and content over time.

Example 3 Example of Administration Method

The mitoxantrone liposomes (specification: 10 mg/10 ml/vial) obtained as above was dissolved in 250 ml of 5% glucose injection, and the drip period was 60 min. Intravenous drip was carried out on forearm at one side, and the semi-recumbent position was adopted during administration. The whole process of intravenous administration was supervised by clinicians.

Example 4 Treatment of DLBCL by Using Mitoxantrone Liposomes Alone Inclusion Criteria A phase II clinical study of mitoxantrone liposomes for treating DLBCL and peripheral T/NK cell lymphoma was conducted. The inclusion criteria for this study is as follows:
1) voluntarily underwent the test and signed informed consent;
2) aged 18 to 75 years, with no gender limitations;
3) ECOG score 0-2 grade;
4) expected survival time ≥3 months;
5) non-Hodgkin's lymphomas of diffuse large B-cells and peripheral T/NK cells are confirmed by histopathology, wherein peripheral T/NK cell lymphomas are limited to the following types: peripheral T-cell lymphoma (non-specific type), angioimmunoblastic T-cell lymphoma, ALK+systemic anaplastic large T-cell lymphoma, ALK- systemic anaplastic large T-cell lymphoma, extranodal NK/T-cell lymphoma, nasal-type, enteropathy-associated T-cell lymphoma, primary hepatosplenic γδ T-cell lymphoma, and subcutaneous panniculitis-like T-cell lymphoma;
6) patients who have experienced at least one systemic treatment failure or recurrence in the past and cannot undergo autologous peripheral blood hematopoietic stem cell transplantation;
7) there is at least one measurable lesion, and the long diameter of a single measurable lesion is ≥1.5 cm;
8) the target tumor is at least 4 weeks apart from the last chemotherapy, radiotherapy, biological therapy, stem cell transplantation or other experimental drug treatment;
9) subjects of childbearing age agree to take effective contraceptive measures during the trial; blood pregnancy test results of females are negative (except for postmenopausal or surgery induced infertility);
10) the level of organ function is basically normal.

Safety Evaluation:

Safety assessment includes adverse events, physical examination and other tests (blood routine, urine routine, blood biochemistry, electrocardiogram, UCG), and early withdrawal due to safety or tolerance reasons. Safety evaluation standard: NCI-CTC4.0.

Effectiveness Evaluation:

Efficacy evaluation method: the patients underwent a tumor evaluation during the baseline period, and the CT scan results of the tumor site should prevail. Efficacy evaluation was conducted according to the standards of the International Workshop Criteria (IWC) for Malignant Lymphoma (2007).

Effectiveness Analysis:

In this study, we analyzed patients with DLBCL. Subjects received an average of 3.0±2.0 cycles of drugs for treatment. Mitoxantrone liposomes were administered at a dosage of 16 mg/m$^2$ or 20 mg/m$^2$ once per 28 days. Of the 19 DLBCL patients with evaluable efficacy, 10 achieved CR or PR, with an ORR of 52.6%.

The ORR of the combination chemotherapy regimen is about 60%-70% (ICE regimen: the combination of three drugs, i.e. ifosfamide, carboplatin, and etoposide has an ORR of 66%; the combination of five drugs, i.e. rituximab, etoposide, methylprednisolone, cytarabine and cisplatin has an ORR of 73%) (Treatment challenges in the management of relapsed or refractory non-Hodgkin's lymphoma—novel and emerging therapies, Journal of Cancer Management and Research, Mark P Chao et al., 2013, Vol. 5, pp. 251-269), which is equivalent to the efficacy of mitoxantrone liposomes used alone in this Example, and there is no statistical difference.

The efficacy of mitoxantrone liposomes clinically used alone for treating DLBCL is shown in Table 5 below in details.

TABLE 5

Efficacy of mitoxantrone liposomes clinically used alone for treating DLBCL

| No. | Dosage (mg/m$^2$) | Number of administration cycles | Previous history of chemotherapy | Best efficacy |
|---|---|---|---|---|
| 1 | 20 | 1 | CHOP × 3<br>DICE × 2<br>Gemox × 4 | PR |
| 2 | 20 | 5 | CHOP × UK | PR |
| 3 | 16 | 6 | HLX01/R-CHOP × 6 | PR |
| 4 | 16 | 2 | HLX01/<br>R-CHOP × 6<br>EP × 2<br>etoposide × UK | PD |
| 5 | 16 | 4 | CHOP × 4 | PR |
| 6 | 20 | 2 | R-CHOP +<br>ibrutinib × 5<br>ICE × 2 | SD |
| 7 | 16 | 2 | R-EPOCH × 6<br>DICE × 6 | SD |
| 8 | 16 | 2 | R-CHOP × 6<br>FC × UK | PD |
| 9 | 16 | 2 | R-CHOP × 1<br>CHOP × 2<br>ICE × 2<br>GCP × 1<br>CHOP +<br>Mesna × 1 | PD |
| 10 | 16 | 2 | R-MTX × 2<br>R-CHOP × 6<br>GEMOX +<br>TNF × 4<br>FC × 1 | PD |
| 11 | 16 | 2 | CHOP × 6<br>CHOP × 4<br>ECOP × 2<br>CTP × 1<br>EPP × 4<br>EP × 1 | PR |
| 12 | 16 | 1 | OB × 3<br>CHOP × 4<br>ABVD × 2 | PD |
| 13 | 16 | 6 | R-CHOP × 6 | CR |
| 14 | 16 | 2 | CDOP × 7<br>GDP × 1<br>DICE × 4 | PR |
| 15 | 16 | 1 | R-CHOP × 6<br>DICE +<br>Chidamide × 3 | PD |

TABLE 5-continued

Efficacy of mitoxantrone liposomes clinically used alone for treating DLBCL

| No. | Dosage (mg/m$^2$) | Number of administration cycles | Previous history of chemotherapy | Best efficacy |
|---|---|---|---|---|
| 16 | 16 | 5 | R-CHOP × 4<br>R-DA-EPOCH × 4<br>GDE × 4<br>R-GDP × 1<br>R-GDP × 4<br>R × UK<br>R-GDE × 2 | PR |
| 17 | 16 | 6 | CHOP × 4<br>DICE × 5<br>R-NP × 3 | PR |
| 18 | 16 | 1 | R-CHOP × 4<br>R-EPOCH × 2 | PD |
| 19 | 16 | 6 | CHOP × 6<br>Gemox × 3 | PR |

Note: the meanings of the above abbreviations are as follows:
CR: complete remission, defined as the disappearance of all evidences of disease.
PR: partial remission, defined as measurable lesion shrinkage without new lesion.
PD: progression of disease, defined as the appearance of any new lesion, or an increase of ≥50% compared with the lowest point of the original lesion.
SD: stable disease, defined as not belonging to any of the situations.
Overall remission rate (ORR) = (CR + PR)/total number of evaluable cases * 100%

CR: complete remission, defined as the disappearance of all evidences of disease.

PR: partial remission, defined as measureable lesion shrinkage without new lesion.

PD: progression of disease, defined as the appearance of any new lesion, or an increase of ≥50% compared with the lowest point of the original lesion.

SD: stable disease, defined as not belonging to any of the situations.

Overall remission rate (ORR)=(CR+PR)/total number of evaluable cases*100%

Example 5 Analysis of Adverse Reactions of Mitoxantrone Liposomes Used Alone for Treating DLBCL Safety Analysis:

The adverse reactions occurred in the above-mentioned DLBCL subjects were analyzed, and the most frequent adverse reaction was hematological toxicity.

As for the hematological toxicity, 31.4% of subjects developed grade 3 or higher leukopenia, 28.6% of the subjects developed grade 3 or higher neutropenia, and 5.7% of the subjects developed grade 3 or higher thrombocytopenia. This is much lower than the hematological toxicity disclosed in the reference analyzed in the background art (Phase II study of the irinotecan (CPT-11), mitoxantrone and dexamethasone regimen in elderly patients with relapsed or refractory peripheral T-cell lymphoma, Journal of Cancer Sci, Nozomi Niitsu et al., 2007, Vol. 98, pp. 109-112) (in this study, 18 cases (60%) developed grades 3-4 hematological toxicity. 8 cases (27%) developed grade 4 neutropenia despite the use of leucocyte increasing agents (G-CSF). 5 cases (16.7%) developed grades 3-4 thrombocytopenia).

As for the non-hematological toxicity, 5.7% of subjects developed grade 3 or higher hypoalbuminemia, 5.7% of subjects developed grade 3 or higher lung infections, 2.9% of subjects developed grade 3 or higher intestinal obstruction, and 2.9% of subjects developed grade 3 loss of appetite.

Example 6 Treatment of PTCL with Mitoxantrone Liposomes Used Alone

The inclusion criteria, administration method, safety and efficacy evaluation are the same as in Example 1.

The mitoxantrone liposomes developed by our company is considered as a second-line treatment for treating PTCL. The ORR of this product in clinical study is 52.9%, which is much higher than those of the HDAC inhibitors including pralatrexate, romidepsin, belinostat, chidamide and the like currently recommended as second-line treatments (HDAC inhibitors are oral preparations and administered once a day. All of the ORR are lower than 30%). Patients who achieve remission in a short period of time can undergo bone marrow transplantation in time.

Mitoxantrone liposomes are injections, which are used at the dosages of 14, 16, 20 mg/m$^2$ or 24 mg/m$^2$, and are administered once per 28 days. The subjects in this study received an average of 3.6±1.8 cycles of treatment.

The efficacy of mitoxantrone liposomes clinically used alone for treating PTCL is shown in Table 6 below in details.

TABLE 6

Efficacy of mitoxantrone liposomes clinically used alone for treating PTCL

| No. of the patient | Dosage (mg/m$^2$) | Number of administration cycles | Previous history of chemotherapy | Best efficacy |
|---|---|---|---|---|
| 1 | 14 | 3 | CHOEP × 3<br>CHOP × 4<br>DICE × 4 | CR |
| 2 | 24 | 2 | Gemcitabine × 4<br>CHOP × 4,<br>GDP × 2 | PD |
| 3 | 20 | 6 | CHOP +<br>LASPAR × 3<br>GEMOX × 2<br>Chidamide × 2<br>GEMOX × 2 | PR |
| 4 | 20 | 5 | CHOPE × 5 | PR |
| 5 | 20 | 3 | CHOPE/GDP × 6,<br>Pralatrexate × 5 | PR |
| 6 | 20 | 2 | CHOP × 4,<br>COP +<br>Lenalidomide × 1<br>D-RPOCH × 1<br>DA-EPOCH × 1 | NA (withdrawal) |
| 7 | 20 | 6 | CHOP × 6 | PR |
| 8 | 16 | 6 | CHOP × 6<br>DICE × 3<br>DHAP × 1 | PR |
| 9 | 16 | 2 | CHOP × 1<br>EPOCH × 6<br>GDP × 6<br>DICE +<br>Thalidomide × 2<br>Pralatrexate × 9 | NA (withdrawal) |
| 10 | 16 | 2 | CHOPE/GDP × 4<br>DICE × 1<br>CE × 4<br>CTX +<br>VP-16 × 5<br>EPOCH × 2 | SD |
| 11 | 16 | 3 | CHOP × 7 | SD |
| 12 | 16 | 2 | CHOPE × 4 | SD |
| 13 | 16 | 6 | CHOP × 7 | PR |
| 14 | 16 | 3 | CHOP × 4<br>ECHOP × 2 | PR |
| 15 | 16 | 5 | Asparaginase +<br>CHOP × 2<br>CHOP × 1<br>Pegaspargase +<br>CHO × 3<br>CHOP × 2 | SD |
| 16 | 16 | 4 | CHOP × 1<br>R-mini-chop × 1<br>CHOP × 1<br>R-CHOP × 4 | PR |
| 17 | 16 | 1 | AEOPP × 1<br>CHOP × 4 | PD |

Note: among them, the meanings of CR, PR, PD, SD, ORR, efficacy evaluation method and efficacy evaluation standard are as described in the "Note" part of Table 5.

Example 7 Analysis of Adverse Reactions of Mitoxantrone Liposomes Used Alone for Treating PTCL The adverse reactions occurred in 15 patients with PTCL were analyzed, and the most frequent adverse reaction was hematological toxicity.

As for the hematological toxicity, 9 subjects (60.0%) developed grade 3 leukopenia, 3 subjects (20%) developed grade 4 leukopenia; 7 subjects (46.7%) developed grade 3 neutropenia, 1 subject (6.7%) developed grade 4 neutropenia; 1 subject developed grade 3 thrombocytopenia; 1 subject developed grade 3 reduction in hemoglobin; and 1 subject developed grade 3 erythropenia.

As for the non-hematological toxicity, no toxicity of grade 3 or higher has occurred.

By comparison, although the incidences of grades 3-4 hematological toxicity were similar, the incidences of grade 4 neutropenia and grades 3-4 thrombocytopenia were all lower than the CMD regimen reported in the previous reference.

The invention claimed is:

1. A method for treating lymphoma, comprising administering to a subject in need thereof a liposomal pharmaceutical preparation of mitoxantrone as a single anti-tumor therapeutic agent, wherein: the liposomal pharmaceutical preparation of mitoxantrone comprises mitoxantrone liposomes,
the mitoxantrone liposomes have a particle size of about 30-80 nm, and comprise mitoxantrone as an active ingredient, wherein mitoxantrone and a multivalent counter ion within the liposomes form a poorly soluble precipitate, the phospholipid bilayer of the liposomes comprises a phospholipid with a phase transition temperature (Tm) higher than body temperature, so that the phase transition temperature of liposomes is higher than the body temperature; and
the lymphoma is relapsed or refractory diffuse large B-cell lymphoma or peripheral T-cell lymphoma.

2. The method of claim 1, wherein the phospholipid with a Tm higher than body temperature is selected from phosphatidylcholine, hydrogenated soybean phosphatidylcholine, hydrogenated egg yolk phosphatidylcholine, dipalmitoyl phosphatidylcholine, distearoyl phosphatidylcholine and any combination thereof; and/or the liposomes have a particle size of about 40-70 nm.

3. The method of claim 1, wherein the phospholipid bilayer contains hydrogenated soybean phosphatidylcholine, cholesterol, and polyethylene glycol 2000-modified distearoylphosphatidylethanolamine at a mass ratio of 3:1:1, and/or the liposomes have a particle size of about 60 nm, and/or the counter ion is sulfate ion.

4. The method of claim 1, wherein the subject has diffuse large B-cell lymphoma and at least has received a first-line and/or second-line treatment, or the subject has peripheral T-cell lymphoma and at least has received a first-line treatment.

5. The method of claim 1, wherein the liposomal pharmaceutical preparation of mitoxantrone is administered once per 3-6 weeks; and/or
the liposomal pharmaceutical preparation of mitoxantrone is administered to the subject 2, 3, 4 or 5 times; and/or
the liposomal pharmaceutical preparation of mitoxantrone is administrated to the subject at a dosage of 14-24 mg/m$^2$.

6. The method of claim 1, wherein the liposomal pharmaceutical preparation is administered to the subject via intravenous drip, and the administration period via drip is 40-80 min.

7. The method of claim 1, wherein the total dosage of the liposomal pharmaceutical preparation administered to the subject is not more than 200 mg/m$^2$.

8. The method of claim 1, wherein the route of administration is selected from oral administration, local administration, subcutaneous injection, intramuscular injection, intravenous drip and intravenous bolus injection.

9. The method of claim 1, wherein the route of administration is intravenous drip, and the method comprises dissolving the mitoxantrone liposomes in sodium chloride injection or glucose injection, and then administering to the subject; wherein the concentration of sodium chloride injection is 0.5%-1%; the concentration of glucose injection is 1%-10%.

10. The method of claim 1, comprising formulating the mitoxantrone liposomes into a solution that can be directly infused before administering to the subject, wherein the concentration of the formulated solution of liposomes that can be directly infused is 0.05 mg/ml-0.5 mg/ml.

11. The method of claim 1, comprising administering to the subject the liposomal pharmaceutical preparation of mitoxantrone 3 or more times for treatment, and the method achieves a higher overall remission rate than a histone deacetylase inhibitor used alone.

12. The method of claim 1, comprising administering to the subject the liposomal pharmaceutical preparation of mitoxantrone 3 or more times for treatment, and the overall remission rate of the method is at least 30%.

13. The method of claim 2, wherein the liposomes have a particle size of 60 nm.

14. The method of claim 5, wherein the liposomal pharmaceutical preparation of mitoxantrone is administered once per 4 weeks.

15. The method of claim 6, wherein the administration period via drip is 60 min.

* * * * *